United States Patent [19]

Novy

[11] Patent Number: 4,942,248

[45] Date of Patent: Jul. 17, 1990

[54] TERTIARY-ALKYL ESTERS OF 1H-BENZOTRIAZOLE-1-CARBOXYLIC ACIDS

[75] Inventor: Paul M. Novy, Roselle, Ill.

[73] Assignee: PPG Industries, Inc., Pittsburgh, Pa.

[21] Appl. No.: 278,691

[22] Filed: Dec. 1, 1988

[51] Int. Cl.$^5$ ............................................. C07D 249/18
[52] U.S. Cl. ................................... 548/533; 548/260; 548/261; 548/344; 548/496; 562/455; 562/567; 562/570; 562/573
[58] Field of Search ............... 548/260, 261, 533, 344, 548/496; 562/567, 445

[56] References Cited

U.S. PATENT DOCUMENTS

| | | | |
|---|---|---|---|
| Re. 30,752 | 9/1981 | Itoh | 548/259 |
| 3,243,423 | 3/1966 | Beyerman | 562/567 |
| 3,725,380 | 4/1973 | König et al. | 548/259 |
| 3,732,238 | 5/1973 | Baker | 548/261 |
| 4,240,822 | 12/1980 | Diehl et al. | 548/261 |
| 4,256,881 | 3/1981 | Simons et al. | 548/261 |
| 4,484,001 | 11/1984 | Krogh | 548/533 |
| 4,500,726 | 2/1985 | Krogh | 548/533 |
| 4,652,665 | 3/1987 | Barcelo et al. | 556/437 |
| 4,710,262 | 3/1987 | Weed | 548/260 |
| 4,741,987 | 5/1988 | Tohda et al. | 548/260 |
| 4,782,164 | 11/1988 | Barcelo et al. | 548/259 |
| 4,837,332 | 6/1989 | Chou | 548/321 |

OTHER PUBLICATIONS

Chem Abstr vol. 94 Entry 59426n (1981).
H. A. Staab, *Angewandte Chemie*, International Edition, vol. 1, pp. 351-367 (1962).
H. A. Staab et al, *Newer Methods of Preparative Organic Chemistry* (Edited by W. Foerst), vol. V, pp. 61-108 (1968).
I. Butula, *Croatica Chemica Acta*, vol. 49, pp. 837-842.
E. Wunsch et al, *Synthesis*, Communications, Nov. 1986, pp. 958-960.
G. Bram, *Tetrahedron Letters*, vol. 6, pp. 469-472 (1973).
J. Singh et al, *Journal of Organic Chemistry*, vol. 53, No. 1, pp. 205-208 (1988).

Primary Examiner—Donald G. Daus
Attorney, Agent, or Firm—George D. Morris

[57] ABSTRACT

Tertiary-butyl and tertiary-amyl esters of 1H-benzotriazole-1-carboxylic acids are useful blocking agents for blocking the amino or imino groups of amino acids. The six-membered ring of the blocking agent may be unsubstituted or substituted with one or more minor substituents.

6 Claims, No Drawings

TERTIARY-ALKYL ESTERS OF 1H-BENZOTRIAZOLE-1-CARBOXYLIC ACIDS

BACKGROUND OF THE INVENTION

Amino acids are often employed as raw materials in the preparation, by a sequence of reactions, of compounds having various uses. In many of these sequences as for example peptide synthesis, it is necessary to reversibly block an amino or imino group of a salt of the amino acid in order that the blocked compound may undergo further reactions which would otherwise irrevocably destroy the amino or imino group, and yet permit later regeneration of the amino or imino group.

The benzyloxycarbonyl group (also known as the carbobenzoxy group or the (phenylmethoxy)carbonyl group) has been extensively used for this purpose. The benzyloxycarbonyl group may be introduced by reacting a salt of the amino acid with a benzyl haloformate such as benzyl chloroformate or benzyl bromoformate. The blocked amino acid salt may then be reacted to form reaction products in which the amino or imino group remains blocked. In most cases, it is eventually desired to remove the benzyloxycarbonyl group and regenerate the amino or imino group. However, the benzyloxycarbonyl group is not easily removed under mild conditions. Consequently, hydrogenation is customarily used for this purpose. Hydrogenation is not a desirable reaction to carry out since it employs hydrogen which is extremely flammable and since it usually employs a catalyst such as palladium on carbon or Raney nickel. A further disadvantage of the hydrogenation process is that toluene is left in the reaction mixture as a contaminant.

Use of the tertiary-butoxycarbonyl group (also known as the 1,1-dimethylethoxycarbonyl group) possesses several advantages over use of the benzyloxycarbonyl group as the blocking group. One such advantage is that the tertiary-butoxycarbonyl group may be removed and the amino or imino group regenerated by treatment with strong acid to a pH of about 1 or less under mild temperature conditions. Another advantage is that the by-products of the tertiary-butoxycarbonyl group upon removal are isobutene (viz., 2-methylpropene) and carbon dioxide, which are both gasses and therefore easily removed from the reaction mixture. The principal disadvantages center on introduction of the tertiary-butoxycarbonyl group. Di-tertiary-butyl dicarbonate,

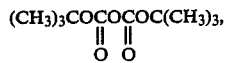

has been used for this purpose, but the compound is very expensive and contributes only one tertiary-butoxycarbonyl group for blocking purposes; the remaining portion of the molecule reacts to form carbon dioxide and either tertiary-butanol or isobutene. Another group of compounds, the unsubstituted or ring-substituted tertiary-butyl phenyl carbonates, have also been employed but the yields are generally low and a by-product of the reaction is the corresponding phenol which is difficult to remove from the reaction mixture. Yet other compounds that have been employed include tertiary-butoxycarbonylazide, tertiary-butoxycarbonylfluoride, 1-tertiary-butoxycarbonyl-1,2,4- triazole, 1-(tertiary-butoxycarbonyl) imidazole, and 1-tertiary-butoxycarbonyl-3-methylimidazolium salts.

THE INVENTION

1H-Benzotriazole-1-carboxylic acid, tertiary-butyl ester, has been synthesized and found to be useful as a blocking agent for salts of amino acids. Several advantages may be realized from this compound, both as to its preparation and as to its use as a blocking agent.

Advantages favoring the preparation of 1H-benzotriazole-1-carboxylic acid, tertiary-butyl ester, include the facile preparation of its precursor, 1H-benzotriazole-1-carbonyl chloride [CAS 65095-13-8]1 in high yields from 1H-benzotriazole [CAS 95-14-7]and phosgene [CAS 75-44-5]; see I. Butula et al, Croatica Chemica Acta. volume 49, pages 837-842 (1977), the entire disclosure of which is incorporated herein by reference. This result, if not unique, is rare because the direct reaction of phosgene with substantially all other common diazoles and triazoles leads to formation of the corresponding carbonylbis(azole) and the corresponding azole hydrochloride and no further reaction. 1H-Benzotriazole-1-carboxylic acid, tertiary-butyl ester, may in turn be advantageously prepared in good yield by reacting 1H-benzotriazole-1-carbonyl chloride with tertiary-butyl alcohol [CAS 75-65-0].

An advantage in using 1H-benzotriazole-1-carboxylic acid, tertiary-butyl ester, as a blocking agent is that the blocking reaction may ordinarily be conducted in the presence of a wide variety of substantially inert solvent systems, such as aqueous systems, aqueous and organic systems, and substantially anhydrous organic systems. Another is that although the cation (or cations, if the amino acid salt has more than one carboxylate group) may contain a nitrogen cationic atom, it need not do so; the cation may be a simpler cation such as an alkali metal cation or an alkaline earth metal cation.

The tertiary-amyloxycarbonyl group functions similarly to the tertiary-butoxycarbonyl group as a blocking group and it possesses analogous advantages over the benzyloxycarbonyl group. The gaseous by-products of removal of the tertiary-amyloxycarbonyl group are 2-methyl-2-butene and carbon dioxide. It is therefore expected that 1H-benzotriazole-1-carboxylic acid, tertiary-amyl ester, may be synthesized by reacting 1H-benzotriazole-1-carbonyl chloride with tertiary-amyl alcohol [CAS 75-85-4]and used as a blocking agent in manners analogous to those pertaining to 1H-benzotriazole-1-carboxylic acid, tertiary-butyl ester.

It is also expected that 1H-benzotriazole-1-carboxylic acid, tertiary-alkyl ester, having one or more minor substituents present on the six-membered ring will be useful as blocking agent for amino acids. Illustrative of the minor substituents are methyl, chloro, and nitro groups. Examples of these substituted compounds include the tertiary-butyl and tertiary amyl esters of 4-methyl-1H-benzotriazole-1-carboxylic acid, and 5-methyl-1H-benzotriazole-1-carboxylic acid, 5,6-dimethyl-1H-benzotriazole-1-carboxylic acid, 5-chloro-1H-benzotriazole-1-carboxylic acid and 5-nitro-1H-benzotriazole-1-carboxylic acid. Irrespective of whether the six-membered ring is unsubstituted or substituted, the valence of each of the three nitrogen atoms in the five-membered ring is three.

Accordingly one embodiment of the invention is 1H-benzotriazole-1-carboxylic acid, tertiary-butyl ester wherein the six-membered ring is unsubstituted or substituted with one or more minor substituents and wherein the valence of each of the nitrogen atoms in the five-membered ring is three.

Another embodiment of the invention is 1H-benoztriazole-1-carboxylic acid, tertiary-amyl ester, wherein the six-membered ring is unsubstituted or substituted with one or more minor substituents and wherein the valence of each of the three nitrogen atoms in the five-membered ring is three.

Yet another embodiment of the invention is a process comprising reacting amino acid salt having at least one unblocked amino or imino group with tertiary-alkyl ester of 1H-benzotriazole-1-carboxylic acid in which the tertiary-alkyl group is tertiary-butyl or tertiary-amyl, to produce the corresponding N-(tertiary-alkoxycarbonyl)-blocked amino acid salt, wherein the six-membered ring of said ester is unsubstituted or substituted with one or more minor substituents and wherein the valence of each of the three nitrogen atoms in the five-membered ring of said ester is three.

A further embodiment of the invention is 1H-benzo-triazole-1-carbonyl chloride wherein the six-membered ring is substituted with or more minor substituents and wherein the valence of each of the three nitrogen atoms in the five-membered ring is three. Illustrative of the minor substituents are methyl, chloro, and nitro groups. Example of these substituted carbonyl chlorides include 4-methyl-1H-benzotriazole1-carbonyl chloride, 5-methyl-1H-benzotriazole-1-carbonyl chloride, 5,6-dimethyl-1H-benzotriazole-1-carbonyl chloride, 5-chloro- 1H-benzotriazole-1-carbonyl chloride, and 5nitro-1H-benzotriazole1-carbonyl chloride.

The unsubstituted or substituted 1H-benzotriazole-1-carbonyl chloride may be prepared by reacting the corresponding unsubstituted or substituted 1H-benzotriazole with phosgene. The reaction is conducted in the presence of substantially inert solvent in which the unsubstituted or substituted 1H-benoztriazole is at least partially soluble.

The solvent is usually a substantially inert organic solvent such as, for example, benzene, ethylbenzene, chlorobenzene, dichlorobenzene, toluene, xylene, chlorinated ethane, chloroform, carbon tetrachloride, methylene chloride, tetrahydrofuran (THF), 1,3-dioxane, and 1,4-dioxane. At least enough substantially inert solvent should be used so that at least a portion of the unsubstituted or substituted 1H-benzotriazole present is dissolved by the solvent. The maximum amount is not governed by theory, but by practical considerations such as cost and the desire to forego processing unnecessarily large amount of solvent.

The proportions of unsubstituted or substituted 1H-benzotriazole and phosgene introduced to the reaction may be about stoichiometric, although an excess of phosgene is preferred.

The temperature employed for the reaction may be considerably varied, but usually they are in the range of from about 20° C. to about 200° C. From about 60° C. to about 150° C. is preferred.

The pressure at which the reaction is conducted is usually about ambient atmospheric pressure or slightly higher, although subatmospheric or substantial superatmospheric pressures may be used.

The unsubstituted or substituted 1H-benzotriazole-1-carbonyl chloride may be recovered from the reaction mixture in which it was formed by any of the various techniques known to the art. Filtration, extraction, precipitation, crystallization, stripping, and drying are some of the techniques which can be used.

The reaction of unsubstituted or substituted 1H-benzo- triazole-1-carbonyl chloride with tertiary-butyl alcohol or tertiary-amyl alcohol is a liquid phase reaction and may be conducted in the presence of substantially inert organic solvent, an acid acceptor, and a catalyst.

The substantially inert organic solvent is preferably substantially nonpolar. Examples of suitable inert organic solvents include n-hexane, n-heptane, cyclohexane, carbon tetrachloride, petroleum ether, methylene chloride, diethyl ether, THF, acetone, and ethyl acetate.

The amines, especially the tertiary amines, may be employed as acid acceptors. Examples of acid acceptors which may be used include the lower trialkylamines such as triethylamine, tripropylamine, diisopropylethylamine, and tributylamine. Other examples include pyridine, methylpyridine, ethylpyridine, 4-(dimethylamino)pyridine, N-methylimidazole, the benzotriazoles, N,N-dimethyl-N-cyclohexylamine, 1,5-diazabicyclo[4.3.0]non-5-ene (DBN), 1,8-diazabicyclo[5.4.0]-undec-7-ene (DBU), 13H-dibenzo[a,i]- carbazole, and 1,1,3,3-tetramethylguanidine (TMG). The preferred acid acceptors are amines, the hydrochlorides of which precipitate from the reaction mixture during the reaction.

Examples of suitable catalysts include pyridine, 4-(dimethylamino)pyridine, N-methylimidazole, DBU, TMG, and DBN.

The proportions of 1H-benzotriazole-1-carbonyl chloride and the tertiary alcohol introduced to the reaction may be about stoichiometric, although a slight excess of the tertiary alcohol is preferred.

The amount of substantially inert organic solvent employed is subject to wide variation. At least enough substantially inert organic solvent should be used so that a liquid phase reaction will proceed. The maximum amount is not governed by theory, but by practical considerations such as cost and the desire to forego processing unnecessarily large amounts of solvent.

The amount acid acceptor, when used, may be widely varied. Usually the ratio of the equivalents of acid acceptor introduced to the equivalents of unsubstituted or substituted 1H-benzotriazole-1-carbonyl chloride introduced is in the range of from about 0.9:1 to about 3:1. From about 1:1 to about 1.2:1 is preferred.

The amount of catalyst may also be widely varied, but usually the ratio of equivalents of catalyst introduced to equivalents of unsubstituted or substituted 1H-benzotriazole-1-carbonyl chloride introduced is in the range of from about 0.1:100 to about 20:100. From about 1:100 to about 5:100 is preferred.

The temperature at which the reaction is conducted may vary considerably but usually the temperature is in the range of from about −20° C. to about +150° C. From about 0° C. to about 100° C. is preferred.

The pressure at which the reaction is conducted is usually about ambient atmospheric or slightly higher, although subatmospheric or substantial supratmospheric pressures may be used.

The tertiary-alkyl ester of the unsubstituted or substituted 1H-benzotriazole-1-carboxylic acid may be recovered from the reaction mixture in which it was formed by any of the various techniques known to the art. Filtration, extraction, precipitation, crystallization, strapping, and drying are some of the techniques which can be used.

Amino acids, the salts of which are used as reactants in the blocking reaction may be widely varied. They may be polypeptides of two, three, four, five, or more fundamental amino acid units. More usually, however, they are the fundamental amino acids themselves. Examples include glycine, alanine, valine, norleucine, leucine, isoleucine, serine, threonine, cysteine, cystine, methionine, arginine, nitroarginine, lysine, ε-(benzyloxycarbonyl)lysine, ornithine, aspartic acid, ε-benzylaspartic acid, glutamic acid, hydroxyglutamic acid, phenylalanine, tyrosine, iodogorgoic acid, thyroxine, tryptophan, proline, hydroxyproline, histidine, canavanine, canaline, citrulline, djenkolic acid, dihydroxyphenylalanine, and 2-thiolhistidine. The amino acids may individually have the L-configuration or the D-configuration, although the L-configuration is more common. Mixtures of amino acids, including racemic mixtures, may also be used.

The amino acid salt used as a reactant in the third embodiment of the invention may be from any source. More usually, however, the salt is prepared in situ by reacting the amino acid with the desired base.

Examples of alkali metal bases that can be used include sodium hydroxide, potassium hydroxide, and lithium hydroxide. Examples of alkaline earth metal bases that can be used include calcium hydroxide and magnesium hydroxide.

The nitrogenous base which can be reacted with the amino acid to form the amino acid salt can be widely varied. Ammonia can be used, but it is preferred that the base be such that the nitrogen cationic atom of the cation of the amino acid salt be directly bonded to at least one carbon atom. Examples of classes of nitrogenous bases that can be used include primary amines, secondary amines, tertiary amines, quaternary ammonium hydroxides, amidines, guanidines, and the pyridines. These are only illustrative and there are numerous other classes of nitrogenous bases that can be used. Examples of nitrogenous bases that can be used include triethylamine, diisopropylethylamine, tetramethylammonium hydroxide, tetramethylammonium methoxide, benzyltrimethylammonium hydroxide, tetraethylammonium hydroxide, DBN, DBU and TMG.

One base or a plurality of bases may be used as desired.

The blocking reaction between amino acid salt having at least one unblocked amino or imino group with tertiary-alkyl ester of unsubstituted or substituted 1H-benzotriazole-1-carboxylic acid occurs in the liquid phase. Although the blocking reaction may in some instances be conducted in the absence of substantially inert solvent, that is, in the melt, it is usually conducted in the presence of substantially inert solvent which serves to dissolve the reactants at least to the degree that the blocking reaction may proceed in the liquid phase. The essential characteristics of the solvent are that it be liquid at the temperature of the blocking reaction, that it be substantially inert to the reactants and products of the blocking reaction, and that it solubilize the reactants at least to the degree that a liquid phase blocking reaction can occur. If any solvent species which do react with the reactants or products of the blocking reaction are present, they are present in very small quantities relative to the nonreactive solvent species. In most cases the substantially inert solvent contains less than about 5 parts of reactive solvent species per thousand parts of the substantially inert solvent, by weight. It is preferred that no reactive solvent species be present.

Examples of substantially inert solvents which can be used with alkali metal salts or alkaline earth metal salts of amino acids include N,N-dimethylformamide (DMF), water, water and DMF, water and 1,4-dioxane, water and 1,3-dioxane, water and THF, water and acetone,, water and methanol, water and ethanol, water and isopropanol, water and N-methylpyrrolidone (NMP), water and tetramethylurea (TMU), and water and N,N'-dimethylimidazolodinone. If the reactants are not sufficiently soluble in the solvent as formulated, their solubilities may be increased by adding water.

Examples of substantially inert solvents which may be used with nitrogenous salts of amino acids include the substantially inert polar aprotic organic solvents having a dielectric constant at 25° C. of at least about 4. Usually the dielectric constant at 25° C. is at least about 10. Often the dielectric constant at 25° C. is at least about 25° C. It is preferred that inert solvent have a dielectric constant at 25° C. of at least about 35. Examples of such solvents which can be used include dimethyl sulfoxide (DMSO), acetonitrile, DMF, THF, methylene chloride, chloroform, nitrobenzene, chlorobenzene, ortho-dichlorobenzene, meta-dichlorobenzene, p-chlorotoluene, 1,1,2,2-tetramethylurea, sulfolane, ethyl acetate, 4-methyl-2-pentanone, benzonitrile, propionitrile, N-methylpropionamide, NMP, ethyl cyanoacetate, acetone, nitromethane, butyronitrile, isobutyronitrile, 2-butanone, ethyl formate, methyl acetate, nitroethane, 1-chloropropane, 2-chloropropane, valeronitrile, 3-pentanone, N,N-dimethylacetamide, methyl propionate, propyl formate, valeronitrile, 1-nitropropane, 2-nitropropane, 1-chlorobutane, 2-chlorobutane, 1-chloro-2-methylpropane, 2-chloro-2-methylpropane, capronitrile, 4-methylvaleronitrile, cyclohexanone, 1,1-dichloroethane, 1,2-dichloroethane, methyl cyanoacetate, ethyl propionate, isobutyl formate, methyl butyrate, ethyl cyanoacetate, butyl acetate, ethyl butyrate, isobutyl acetate, toluic nitrile, 2-methoxyethyl acetate, capronitrile, ethyl acetoacetate, 1,1,1-trichloroethane, and e(hylene diacetate.

Only one substantially inert solvent or a mixture of such solvents may be used as desired.

In the preferred embodiment where the salt-forming reaction is conducted in a substantially inert solvent system, the amount of substantially inert solvent present is sufficient to dissolve at least a portion of the amino acid salt produced. Preferably the amount of such solvent present is sufficient to dissolve all of the amino acid salt produced. The maximum amount of substantially inert solvent used is not governed by theory, but by practical considerations such as the quantities of liquid that must be handled and whether or not the amino acid salt is to be recovered prior to reaction with the blocking agent or reacted in situ with the blocking agent. Usually the weight ratio of the substantially inert solvent to the amino acid having at least one unblocked amino group initially present in the salt-forming reaction is at least about 3:1. In many cases the weight ratio is in the range of from about 3:1 to about 25:1. Preferably the weight ratio is in the range of from about 5:1 to about 20:1.

Similarly, the amount of substantially inert solvent present during the blocking reaction may also vary widely. In general, sufficient substantially inert solvent should be present so that the blocking reaction may be conducted in the liquid phase. Although it is necessary only that a portion of the amino acid salt be initially dissolved in the substantially inert solvent, it is preferred that all of the amino acid salt be dissolved prior to beginning the blocking reaction. The maximum amount of substantially inert solvent that can be present is not governed by theory, but by practical considerations used as the quantities of liquid that must be handled and the ease with which the product may be recovered. Ordinarily the weight ratio of substantially inert solvent to the amino acid salt having at least one unblocked amino group initially present is at least about 1:1. Often the weight ratio is in the range of from about 1:1 to about 20:1. Preferably the weight ratio is in the range of from about 2:1 to about 10:1.

The equivalent ratio of the base to the amino acid introduced to the salt-forming reaction may be widely varied, but typically it is in the range of from about 0.9:1 to about 5:1. Often the equivalent ratio is in the range of from about 1:1 to about 3:1. An equivalent in the range of from about 1:1 to about 1.5:1 is preferred.

When the base is one that would significantly react with the blocking agent, it should be used in about stoichiometric proportions with the amino acid or the excess should be substantially removed prior to the blocking reaction. If the nitrogenous base is not significantly reactive with the blocking agent as is preferred, the excess, if any, may be retained in the system.

The equivalent ratio of the blocking agent to the amino acid salt introduced to the blocking reaction is similarly susceptible to wide variation. Ordinarily the equivalent ratio is in the range of from about 0.9:1 to about 3:1. Often the equivalent ratio is in the range of from about 1:1 to about 2:1. An equivalent ratio in the range of from about 1.1:1 to about 1.7:1 is preferred.

The temperature at which the salt forming and blocking reactions are conducted may vary considerably, but ordinarily they are in the range of from about the freezing point of the system to about 100° C. Typically the temperatures are in the range of from about −10° C. to about +70° C. Temperatures in the range of from about 10° C. to about 50° C. are preferred.

The pressures at which the salt forming and blocking reactions are conducted may also be widely varied. Atmospheric and slightly superatmospheric pressures are generally employed, although greater or lesser pressures may be used.

The reactions may be carried out batchwise, continuously, semibatchwise or semicontinuously.

The blocked amino acid salt may be recovered from the reaction mixture in which it was formed by any of the various techniques known to the art. Water washing, extraction, precipitation, stripping, and drying are examples of some of the techniques which can be used.

The invention is further described in conjunction with the following examples which are to be considered illustrative rather than limiting, and in which all parts are parts by weight and all percentages are percentages by weight unless otherwise specified.

EXAMPLE I

A 500 milliliter, 1-necked round bottom flask equipped with a magnetic stirring bar was charged with 54.5 (0.30 mole) of 1H-benzotriazole-1-carbonyl chloride, 25.6 grams (0.345 mole) of tertiary-butyl alcohol, and 197.7 grams of n-hexane. The charged materials were stirred to produce a white slurry. One gram (0.0126 mole) of pyridine was added, which caused the slurry to develop a slight yellow color. A 60 milliliter pressure equalizing addition funnel was inserted into the neck of the flask. The addition funnel was charged with 38.0 grams (0.294 mole) of diisopropylethylamine [CAS 7087-68-5] which was added dropwise over a period of about 40 minutes to produce a precipitate. A definite exotherm, which was noticed a few minutes after beginning the addition, continued during the remainder of the addition. After completing the addition, an electric heating mantle was fitted to the reaction flask, but heating was not applied. The reaction mixture was allowed to cool slowly over 2 hours and then allowed to stand unstirred over a weekend. Only partial settling of solids occurred. The reaction mixture was reslurried and then filtered at room temperature in a 350 milliliter fritted disc funnel. The reaction flask and white solids were washed with 75 milliliters of fresh n-hexane in three portions. The n-hexane from the washings was combined with the original filtrate to form a first solution weighing 258.3 grams. Solvent was removed from the first solution under vacuum in a rotary evaporator to a weight of 65.8 grams of crystallized solids and remaining n-hexane. The light yellow solids were collected in a 150 milliliter fritted disc funnel and the mother liquor was saved. The stripping flask and the solids were washed quickly with 30 milliliters of ice-cold n-hexane. The n-hexane from this washing was combined with the saved mother liquor to form a second solution. The solids were dried on the frit under vacuum at 55° C. to 60° C. for 4 hours to produce 32.4 grams of light yellow solids having a melting range of 62° C. to 63° C. as a first crop of product.

Solvent was removed from the second solution under vacuum in a rotary evaporator to produce 3.9 grams of partly wet orange solids as a second crop of product.

The white solids resulting from filtration of the reaction mixture, which solids have been washed with n-hexane as described above, were dried under vacuum to produce 64.8 grams of slightly sticky powder. Of this powder, 60.4 grams was reslurried in 200 grams of n-hexane and warmed on a hot plate to 45° C. The slurry was filtered using a 350 milliliter fritted disc funnel. Flask and solids were washed with 50 milliliters of fresh n-hexane in two portions. The n-hexane from the washings was combined with the original filtrate from the reslurried solids to form a third solution weighing 218.2 grams. Solvent was removed from the third solution under vacuum in a rotary evaporator to produce 3.4 grams of white solids having a melting range of 59.5° C. to 61.5° C. as a third crop of product.

The solids which had been reslurried, filtered and washed as described above were dried under vacuum, but inasmuch as the solids started to melt at about 60° C. heating was discontinued and the oven was allowed to cool slowly overnight while still under vacuum. The extremely deliquescent sticky solid which resulted weighed 56.3 grams.

Analysis of a very concentrated CDCl₃ solution of a sample of the first crop of product confirmed the structure as that of 1H-benzotriazole-1-carboxylic acid, tertiary-butyl ester.

The normalized liquid chromatographic assay of the first crop of product was 98.6 area percent 1H-benzotriazole-1-carboxylic acid, tertiary-butyl ester, and 1.03 area percent 1H-benzotriazole.

Using the first crop of product as a reference internal standard, the relative liquid chromatographic assays of the second and third crops of product were 69.2 area percent and 99.2 area percent 1H-benzotriazole-1-carboxylic acid, tertiary-butyl ester, respectively. Using an independently determined response factor for 1H-benzotriazole, liquid chromatographic analyses showed the second and third crops of product to contain 1.8 and 1.2 weight percent 1H-benzotriazole, respectively.

EXAMPLE II

A 500 milliliter, 3-necked round bottom flask equipped with a magnetic stirring bar, a thermometer, a 125 milliliter addition funnel, and an adapter for nitrogen blanketing was charged with 54.5 grams (0.30 mole) of 1H-benzotriazole-1-carbonyl chloride, 25.0 grams (0.337 mole) of tertiary-butyl alcohol, and 202.3 grams of n-hexane. The addition funnel was charged with 23.7 grams (0.30 mole) of pyridine. The reaction mixture was cooled to 2° C. in an ice bath and the pyridine was added to the reaction mixture according to the schedule of Table 1.

TABLE 1

| Time, hours:minutes | Temperature, °C. | Pyridine in Addition Funnel, milliliters, approx. | Remarks |
|---|---|---|---|
| 0:00 | 2.0 | 25 | Pyridine addition begun. |
| 0:01 | 2.5 | 20 | Pyridine addition stopped. |
| 0:02 | 4.5 | 20 | Pyridine addition resumed. |
| 0:03 | 6 | 15 | |
| 0:05 | 12.5 | 8 | |
| 0:08 | 13 | 0 | Pyridine addition completed. Ice bath removed. |
| 0:12 | 19.5 | | |
| 0:16 | 23.5 | | |
| 0:27 | 27 | | |
| 1:00 | 30 | | |

The reaction mixture was allowed to stand overnight at room temperature. The reaction mixture was filtered with a 350 milliliter fritted disc funnel while the frit was carefully blanketed with a flow of nitrogen gas from above. The reaction flask and filter cake were washed with 150 milliliters of fresh n-hexane in four portions. The n-hexane washings were combined with the mother liquor. Some crystallization occurred in the filter flask before completion of the final washing. The total filtrate weighed 291.9 grams. The solids in the filter flask were broken up with a spatula and then the solvent was removed under vacuum in a rotary evaporator at temperatures up to 40° C. The resulting product was awhite, flowing crystalline powder weighing 46.4 grams. Liquid chromatographic analysis using an internal standard showed the product to contain 100.2 weight percent 1H-benzotriazole-1-carboxylic acid, tertiary-butyl ester and 0.24 weight percent 1H-benzotriazole based on response factors from product in Example I. Nuclear magnetic resonance spectroscopic analysis showed the product to contain no other components.

EXAMPLE III

A 2 liter, 4-necked round bottom flask equipped with a poly(tetrafluoroethylene) blade stirrer, a thermometer, a total reflux condenser, and a 125 milliliter addition funnel was charged with 234.4 grams of melted 1H-benzotriazole-1-carbonyl chloride of 83.2 percent purity (1.074 moles) which contained 0.6 percent HCl, 590.7 grams of n-hexane, and 93.2 grams (1.257 moles) of tertiary-butyl alcohol. The addition funnel was charged with 87.9 grams (1.11 moles) of pyridine. The reaction mixture was cooled to 2.5° C. in an ice bath and the reaction mixture according to the schedule of Table 2.

TABLE 2

| Time, hours:minutes | Temperature, °C. | Pyridine in Addition Funnel, milliliters, approx. | Remarks |
|---|---|---|---|
| 0:00 | 2.5 | 90.5 | Pyridine addition begun. |
| 0:05 | 9.0 | 58 | Ice bath removed. |
| 0:10 | 23 | 35.5 | Heating mantle applied for insulation |
| 0:15 | 35 | 13 | |
| 0:19 | 39 | 0 | Pyridine addition completed. |
| 0:30 | 41.5 | | Some exotherm noted. Heating was begun. |
| 0:40 | 44 | | |
| 0:50 | 54 | | |
| 1:00 | 68.5 | | Moderate reflux. |
| 1:10 | 70 | | Trace of solid sublimation in condenser. |
| 1:25 | 70 | | |
| 1:45 | 70 | | |
| 2:05 | 70 | | Heat off. Cooled in ice bath to 17.5° C. |

The reaction mixture was allowed to stand overnight at room temperature. After heating to 61° C., the reaction mixture was filtered with a warmed 600 milliliter fritted disc funnel. The pyridine hydrochloride solids nearly filled the funnel. The reaction flask and the filter cake were washed with 170 milliliters of n-hexane in three portions with heating of the n-hexane in the reaction flask before cake washing. The n-hexane from the washings was combined with the original filtrate to provide 890.8 grams of yellow solution. The solvent from this solution was removed under vacuum in a rotating evaporator in two portions to yield 236.9 grams of light yellow solids as product.

EXAMPLE IV

A 100 milliliter, 1-necked round bottom flask equipped with a magnetic stirring bar was charged with 3.45 grams (0.03 mole) of L-proline and 6 milliliters of water. The L-proline dissolved almost completely in the water. Six milliliters of 5.0 N aqueous sodium hydroxide solution (0.03 mole NaOH) was pipetted into the flask dropwise. No significant exotherm was observed. The addition of 12 milliliters of 1,4-dioxane caused a very slight endotherm, but the reaction mixture remained a solution.

To the stirred solution of L-proline, sodium salt, was added 7.Z3 grams (0.033 mole) of 1H-benzotriazole-1-carboxylic acid, tertiary-butyl ester, in a single portion. The solid 1H-benzo triazole-1-carboxylic acid, tertiary-butyl ester, became an oil almost immediately which gradually emulsified more and more wi continued rapid stirring. After about 2 minutes the reaction mixture was uniformly hazy and was warm due to an exothermic reaction. After approximately another 2 minutes, the temperature of the reaction mixture reached a maximum of 35° C. and then began to recede. A completely clear yellow solution formed during the exothermic reaction. An electric heating mantle was fitted to the flask to slow the cooling but heating was not applied. No further change in appearance was observed during the next hour. The reaction mixture was allowed to stand overnight. No change in appearance of the clear yellow solution occurred. The pH of the reaction mixture was 8.24.

The magnetic stirring bar was removed from the flask and 11.9 grams of mostly 1,4-dioxane was stripped from the reaction mixture under vacuum in a rotating evaporator. Thereafter 20 milliliters of water was added and the pH was observed to be 8.01. After transfer to a 60 milliliter separatory funnel, the reaction mixture was extracted three times with 20 milliliter portions of fresh methyl tertiary-butyl ether. Most of the yellow color of the reaction mixture was present in the first extract. The second and third extracts were colorless. Only a trace of yellow color remained in the aqueous phase. During all three extractions there was rapid separation of phases with no emulsion at the interface.

The extracted aqueous phase was transferred to a 150 milliliter beaker equipped with a magnetic stirring bar and a pH probe. With rapid stirring the solution was acidified to pH 1.85 with concentrated hydrochloric acid. An insoluble liquid oil phase began to form as the pH reached about 4 during the acidification. A heavy lower liquid phase of oil eventually formed a small lower layer, but much oil was sticking to the side of the beaker. The beaker was placed in an ice bath and its contents were stirred to promote crystallization. After about 15 minutes the ph of the emulsion was increased to 2.9 by dropwise addition of a very small quality of 5N aqueous sodium hydroxide solution. After stirring in the ice bath for about 30 minutes, the oil crystallized to a white solid. Some larger droplets of oil formed large chunks which were broken up as well as possible with a spatula. Stirring was continued in the ice bath for 2 hours. The resulting first crop of white solids was collected in a small fritted disc funnel and the beaker and filter cakewere rinsed with about 20 milliliters of ice water. The first crop was dried on the frit in a vacuum oven at 60° C. to 65° C. for 3 hours. The oven was then turned off and the first crop was left to cool slowly overnight while still under vacuum. The dry first crop weighed 5.6 grams. The melting range of a sample of the first crop was 132.5° C. to 134° C. with slight gas evolution, which is very close to the melting range of 136° C. to 137° C. reported in the literature for N-(tertiary-butyoxycarbonyl)- L-proline (Boc-Pro).

The aqueous mother liquor from which the first crop had crystallized was extracted three times with 25 milliliter portions of methyl tertiary-butyl ether. The extracts were combined and dried over anhydrous magnesium sulfate. Methyl tertiary-butyl ether was removed by stripping until a hazy oil weighing 1.1 grams remained. Normal hexane was added to the oil and the mixture was stirred and shaken until solids crystallized from the oil. The solids were allowed to form over a period of about 2 hours and then they were broken up to more uniform particles. These solids were collected in a small fritted disc funnel and dried in a hot air oven at 55° C. to 60° C. The oven temperature was raised to 65° C. and the formerly white granular solids melted to a thick oil, at which point drying was discontinued. The resulting second crop weighed 0.82 grams.

The methyl tertiary-butyl ether extracts from the original reaction mixture were combined and the solvent was removed under vacuum in a rotating evaporator to produce 3.5 grams of light yellow solid. The solid crystallized spontaneously near completion of stripping.

Samples of the first crop, second crop, and by-product were analyzed by liquid chromatography using internal standards. The results, as compared with samples of commercial Boc-Pro or commercial 1H-benzotriazole, as the case may be, are shown in Table 3.

TABLE 3

| Sample | Concentration, weight percent | | Remarks |
| --- | --- | --- | --- |
| | Boc—Pro | Benzotriazole | |
| First Crop | 103.8 | 0.3 | |
| Second Crop | 52.0 | 14.1 | |
| By-Product | — | 93.5 | No other significant peaks other than the internal standard were present. |

Titration of a sample of the first crop using aqueous sodium hydroxide solution indicated an assay of 101.7 weight percent if pure Boc Pro. The specific rotation of a sample of the first crop (c=1 in acetic acid) was found to be −61.4° as compared with a literature value (c=2 in acetic acid) of −60.2° for Boc-Pro.

EXAMPLE V

A 100 milliliter, 1-necked round bottom flask equipped with a magnetic stirring bar and a thermometer was charged with 3.94 grams (0.030 mole) of L-leucine and 6 milliliters of water. The L-leucine did not dissolve. Following the addition of 6.2 milliliters of 5N aqueous sodium hydroxide solution (0.031 mole NaOH) a complete solution was obtained. The addition of 12 milliliters of 1,4-dioxane caused no apparent change.

As 7.23 grams (0.033 mole) of 1H-benzotriazole-1-carboxylic acid, tertiary-butyl ester, was added, a solid precipitate formed. After the addition had been completed, the solid precipitate became a thick oil and the temperature of the reaction mixture dropped from 29° C. to 26° C. After 5 minutes the temperature had returned to 29° C. and a semi-solid precipitate began to form. The temperature increased to 33° C. after a further 5 minutes and the reaction mixture was thick with solid precipitate which was quite viscous and retained gas bubbles brought in with the stirring. An electric heating mantle was fitted to the flask for insulation purposes but heating was not applied. After a further 10 minutes the temperature reached a maximum of 35° C. The thick precipitate tended to float above the rest of the slurry and stuck to the sides of the flask at the liquid level. If stirring was stopped, all of the precipitate floated to the surface of the reaction mixtures to form a white emulsion layer which was readily reslurried by stirring. After 40 minutes the temperatures had dropped to 33° C. and the thick precipitate remained. Six milliliters of 1,4-dioxane was added to thin the reaction mixture but no solids dissolved. After stirring overnight, most of the thick precipitate had dissolved into the yellow liquid phase of the reaction mixture. The reaction mixture was warmed slowly with the heating mantle to 50° C. and after one hour at 50° C. all the thick floating precipitate had dissolved, but a small quantity of fine white crystals which settled out when stirring was stopped, remained. The reaction mixture was maintained at 50° C. for 3 more hours and some further dissolution seemed to occur, but the reaction mixture never cleared and some of the fine white crystals remained. The solids were filtered from the reaction mixture with a small Hirsch funnel and rinsed with a few milliliters of water. The white crystals seemed to slightly dissolve in the fresh water wash. After drying in an air oven at 60° C. for several hours, the dry crystals weighed 0.18 gram and had a melting point greater than 210° C.

The pH of the clear yellow filtrate from the Hirsch filter was 8.85. In a rotating separator. 32.7 8rams of material was removed under vacuum from the clear yellow filtrate. The aqueous. slightly viscous oil which remained was transferred to a 60 milliliter separating funnel using a little added water to assist the transfer. The aqueous oil was extracted three times with 20 milliliter portions of fresh methyl tertiary-butyl ether. Less color was extracted into the organic phase than was the case in Example III. The aqueous phase was then charged into a 150 milliliter beaker and cooled in an ice bath with magnetic stirring. Concentrated hydrochloric acid was added dropwise while closely observing the pH with a probe and meter. Significant precipitation of solids began occurring at about pH 6 and continued to about pH 3.5. After the pH was lowered to 2.5, a very thick but completely stirring slurry of solids was obtained. After stirring several minutes the slurry thickened further to a non-stirring paste. About 25 milliliters of water had to be added to achieve any stirring at all, but much of the mass was still sticking to the beaker and not stirring. As stirring was continued for 20 minutes in an ice bath the mixture gradually thinned out to form a fairly thin white slurry which was left to stand approximately 40 hours. The pH of the aqueous phase was 2.23. The first crop of solids did not settle very much on standing and were easily reslurried. They appeared to be fine and somewhat pasty physically, but filtered very easily at room temperature and were washed with about 50 milliliters of water. The first crop was dried as much as possible on the frit. The moist solids which weighed 7.6 grams, were then transferred to a 125 milliliter round bottom flask for drying under vacuum in a rotating evaporator to a final weight of 5.62 grams. The first crop had fluffed-up during drying to almost fill the previously half-full flask with very fine light powder. The melting range of a sample of the first crop was 77° C. to 85° C. as compared with a melting range of 78° C. to 81° C. reported in the literature for N-(tertiary-butoxycarbonyl)-L-leucine hydrate (Boc-Leu.H$_2$O).

The mother liquor from the first crop was extracted with methyl tertiary-butyl ether. After phase separation, water was removed from the aqueous phase to yield a second crop weighing 1.74 grams.

The methyl tertiary-butyl ether extracts were combined and the solvent was removed under vacuum in a rotating evaporator to produce 2.5 grams of light yellow solid by-product.

Samples of the first crop, second crop, and by-product were analyzed by liquid chromatography using internal standards. The results are shown in Table 4.

TABLE 4

| Sample | Concentration, weight percent | | Remarks |
|---|---|---|---|
| | Boc—Leu.H$_2$O | Benzotriazole | |
| First Crop | 97.2 | 0.07 | |
| Second Crop | 14.0 | 3.7 | Other components unknown. |
| By-Product | — | 89.0 | No other significant components visible on the LC scan. |

A sample of the first crop was found to contain 7.74 weight percent water as compared with a theoretical value of 7.22 weight percent for Boc-Leu.H$_2$O. The specific rotation of a sample of the first crop was found to be −24.6° as compared with a literature value of −30° for Boc-Leu.H$_2$O.

EXAMPLE VI

A 100 milliliter, 1-necked round bottom flask equipped with a magnetic stirring bar and thermometer was charged with 4.96 grams (0.030 mole) of L-phenylanine and 6.2 milliliters of 5N aqueous sodium hydroxide solution (0.031 mole NaOH). The crystalline L-phenylanine slowly dissolved to form a clean, viscous solution. The addition of 6 milliliters of water greatly thinned the solution. This was followed by the addition of 12 milliliters of 1,4-dioxane.

To the clear solution was added 7.23 grams (0.033 mole) of 1H-benzotriazole-1-carboxylic acid, tertiary butyl ester, in one portion. A thick oil formed as the reaction mixture was stirred. The temperature dropped from 26° C. to 23° C. immediately. After 10 minutes the temperature had returned to 25.5° C. at which time the reaction mixture was a uniformly hazy mixture with no distinct phase separation occurring if stirring was stopped briefly. The reaction flask was insulated with an electric heating mantle but heating was not applied. A very slight exotherm raised the temperature to 29° C. after 40 minutes. After a further 10 minutes at 29° C. the reaction mixture cleared completely to a light yellow solution with no trace of haze present. After stirring for an additional 15 minutes, the stirring was stopped and the reaction mixture was allowed to stand overnight at room temperature. No change inappearance of the reaction mixture occurred. To ensure complete reaction, the clear yellow solution was slowly heated to 50° C. and held at that temperature for 2 hours. Again no change in appearance resulted. The pH of the reaction mixture was 8.7. In a rotating evaporator, 25.0 grams of material was removed under vacuum from the reaction mixture. The very viscous clear yellow oil which remained was diluted with 20 milliliters of water and transferred to a 60 milliliter separating funnel. The aqueous solution was extracted with 20 milliliters of methyl tertiary-butyl ether which removed some of the yellow color from the aqueous phase. The aqueous phase was then extracted five times with 10 milliliter portions of fresh methyl tertiary-butyl ether. The six methyl tertiary-butyl ether extracts were combined and extracted with 10 milliliters of water. The aqueous phase was added to the aqueous phase of the reaction mixture. While stirring the combined aqueous phases in a 150 milliliter beaker in an ice bath, concentrated hydrochloric acid was added dropwise. Most precipitation occurred between pH 5 and pH 4. The pH was lowered to 2.8. A very viscous oil resulted which was stirred in the ice bath for 1 hour. No crystallization was observed. Stirring continued overnight. No change in appearance resulted. Thirty milliliters of methyl-tertiary butyl ether was added to the reaction mixture and the oil slowly dissolved to form a light yellow upper liquid phase. The liquid phases were separated in a 60 milliliter separatory funnel. The aqueous phase was extracted four times with 15 milliliter portions of fresh methyl tertiary-butyl ether with rinsing of the acidification beaker each time to be sure all of the sticky oil was removed.

The combined methyl tertiary-butyl ether extracts were dried over anhydrous magnesium sulfate and then filtered to yield a clear, very light yellow solution. The solvent was removed under vacuum in a rotating evaporator to produce a clear viscous oil weighing 10.2 grams. To the oil was added 33.3 grams of n-hexane and the mixture was stirred as well as possible. A very small quantity of solids obtained by n-hexane trituration of some of the pre-stripped methyl tertiary-butyl ether solution was added to aid crystallization. After about 10 minutes the oil started to solidify and the larger agglomerates were broken up as they formed in the n-hexane. After 2 hours solidification was complete and the larger particles were pulverized with a spatula. The mixture was allowed to stand overnight. Larger particles were then further broken up and the slurry was stirred vigorously for 2 hours. The volatile materials were removed under vacuum in a rotating evaporator using temperatures up to 45° C. to produce 7.7 grams of fine white powder as the product. The melting range of a sample of the product was 75° C. to 80.5° C. as compared with a melting range of 86° C. to 88° C. reported in the literature for N-(tertiary-butoxycarbonyl)- L-phenylalanine (Boc-Phe).

The organic phase resulting from the water extraction of the combined first six methyl tertiary-butyl ether extracts was placed in the flask of a rotating evaporator where solvent was removed under vacuum to produce 2.4 grams of solid by-product.

Sample of the product and the by-product were analyzed by liquid chromatography using internal standards. The results are shown in Table 5.

TABLE 5

| Sample | Concentration, weight percent | |
| --- | --- | --- |
|  | Boc—Phe | Benzotriazole |
| Product | 78.2 | 10.6 |
| By-Product | — | 93.2 |

EXAMPLE VII

A 500 milliliter, 3-necked round bottom flask equipped with a magnetic stirring bar, a thermometer, a dip tube, and a Dewar reflux condenser cooled with acetone and solid carbon dioxide was charged with 51.3 grams (0.385 mole) of 5-methyl-1H-benzotriazole and 200.7 grams of toluene. The charged materials were heated to 45° C. to 50° C. to dissolve all of the solids. Phosgene as introduced below the surface of the liquid via the dip tube according to the schedule of Table 6.

TABLE 6

| Time, hours:minutes | Temperature, °C. | Phosgene Added, grams, cumulative | Remarks |
| --- | --- | --- | --- |
| 0:00 | 44.5 | 0 | Phosgene addition begun. Immediate exotherm. |
| 0:05 | 54 | 6.3 |  |
| 0:10 | 57.5 | 11.8 | Phosgene addition stopped. Dip tube clogged. Some phosgene lost. |
| 0:15 | 57 | 11.8 | Phosgene addition resumed. |
| 0:20 | 58.5 | 17.8 | Exotherm stopped at 60° C. Heating begun. |
| 0:30 | 74 | 28.3 | Strong evolution of HCl. |
| 0:40 | 81.5 | 38 |  |
| 0:50 | 90.5 | 48.4 |  |
| 0:55 | 91.5 | 54.0 | Phosgene addition completed. Slow evolution of HCl. |
| 1:05 | 95 | 54.0 |  |
| 1:20 | 95 | 54.0 |  |
| 1:35 | 95 | 54.0 | Heating stopped. N₂ sparge through dip tube begun. |
| 1:50 | 39 |  | N₂ sparge discontinued. |

The resulting clear orange solution was distilled under vacuum to remove toluene and to form a thin slurry. After standing about 6½ days, the slurry was filtered into a small fritted disc funnel. The reaction flask and filter cake was washed with about 82 grams of n-hexane in three portions. The white solids were dried on the frit under vacuum for 3 hours at 65° C. to 70° C. to produce 22.1 grams of by-product. The melting range of the by-product was 97.5° C. to 104° C. The by-product is believed to be primarily 1,1'-carbonyl-bis(5-methyl-1H-benzotriazole).

Approximately 50 milliliters of n-hexane was added to the filtrate. Solvent was removed from the resulting solution [under vacuum] at 10° C. to 25° C. in a rotating evaporator. As solvent removal progressed, solids formed. After almost all of the n-hexane had been removed, the solids began to reliquify. Normal hexane was recharged to the somewhat viscous, dark brown residue from the solvent stripping and the mixture was cooled with stirring to −10° C. to form a very thick slurry of brown solids. This slurry was filtered in a fritted disc funnel and the flask and the filter cake were washed with about 50 milliliters of ice-cold n-hexane in two portions. Almost all of the brown color rinsed out of the filter cake to yield beige crystalline solids. The solids were dried on the frit under vacuum at 50° C. to 60° C. only long enough for the temperature of the vacuum oven to increase because it appeared that some of the solids were beginning to melt. Upon bottling this first crop of product, it was apparent that some slight melting had occurred. The first crop of the product weighed 24.9 grams and melted in the range of from 58° C. to 63° C. It is believed that the first crop of product was primarily 5-methyl-1H-benzotriazole-1-carbonyl chloride.

The brown mother liquor from isolation of the first crop was cooled in an ice bath to crystallize more solids. The resulting slurry was filtered in a fritted disc funnel under nitrogen gas and rinsed with about 30 milliliters of ice-cold normal hexane. Most of the brown color of the mother liquor accompanied the solids and was not appreciably removed by the n-hexane washing. The solids were dried under vacuum in a cooler oven than was the first crop. Nevertheless, some melting did occur. The resulting second crop of product weighed 13.4 grams and melted in the range of from 47° C. to 78° C. The wide melting range indicates that the second crop of product is quite impure.

Although the present invention has been described with reference to specific details of certain embodiments thereof, it is not intended that such details should be regarded as limitations upon the scope of the invention except insofar as they are included in the accompanying claims.

I claim:

1. A process comprising reacting amino acid salt having at least one unblocked amino or imino group with tertiary-alkyl ester of 1H-benzotriazole-1-carboxylic acid in which the tertiary-alkyl group is tertiary-butyl or tertiary-amyl, to produce the corresponding N-(tertiary-alkoxycarbonyl)-blocked amino acid salt, wherein the six-membered ring of said ester is unsubstituted or substituted with one or two inert minor substituents and wherein the valence of each of the three nitrogen atoms in the five-membered ring of said ester is three.

2. The process of claim 1 wherein the six-membered ring of said ester is substituted with one of two inert minor substituents selected from the group consisting of methyl, chloro, and nitro.

3. The process of claim 1 wherein said ester is 5-methyl-1H-benzotriazole-1-carboxylic acid, tertiary-butyl ester, or 5-methyl-1H-benzotriazole-1-carboxylic acid, tertiary amine ester.

4. The process of claim 1 wherein the six-membered ring of said ester is unsubstituted.

5. The process of claim 1 wherein the six-membered ring is substituted with one or two inert minor substituents selected from the group consisting of methyl and chloro.

6. The process of claim 1 wherein said ester is selected from the group consisting of 4-methyl-1H-benzotriazole-1-carboxylic acid, tertiary-butyl ester; 5,6-dimethyl-1H-benzotriazole-1-carboxylic acid, tertiary-butyl ester; 5-chloro-1H-benzotriazole-1-carboxylic acid, tertiary-butyl ester; 5-nitro-1H-benzotriazole-1-carboxylic acid, tertiary-butyl ester; 4-methyl-1H-benzotriazole-1-carboxylic acid, tertiary amyl ester; 5,6-dimethyl-1H-benzotriazole-1-carboxylic acid, tertiary-amyl ester; 5-chloro-1H-benzotriazole-1-carboxylic acid, tertiary-amyl ester; and 5-nitro-1H-benzotriazole-1-carboxylic acid, tertiary-amyl ester.

* * * * *